(12) United States Patent
Miura et al.

(10) Patent No.: US 6,549,290 B2
(45) Date of Patent: Apr. 15, 2003

(54) METHOD AND APPARATUS FOR ALIGNING TARGET OBJECT

(75) Inventors: Yasutada Miura, Hachioji (JP); Shunsuke Kurata, Kamiina-gun (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/796,287

(22) Filed: Feb. 28, 2001

(65) Prior Publication Data

US 2001/0006571 A1 Jul. 5, 2001

Related U.S. Application Data

(63) Continuation-in-part of application No. 09/400,408, filed on Sep. 21, 1999.

(30) Foreign Application Priority Data

Sep. 22, 1998 (JP) ............................................ 10-268301

(51) Int. Cl.⁷ .............................................. G01B 11/14
(52) U.S. Cl. ...................... 356/614; 356/621; 356/401; 250/559.36
(58) Field of Search ................................ 356/614, 615, 356/621, 622, 624, 399–401; 250/548, 559.29, 559.3, 559.36; 359/383, 393, 397, 368

(56) References Cited

U.S. PATENT DOCUMENTS

| 4,887,904 A | 12/1989 | Nakazato et al. |
| 5,258,823 A | 11/1993 | Akamatsu |
| 5,438,209 A | 8/1995 | Yamamoto et al. |
| 5,499,097 A | 3/1996 | Ortyn et al. |
| 5,917,601 A | 6/1999 | Shimazaki et al. |

FOREIGN PATENT DOCUMENTS

| JP | 2-90117 | 3/1990 |
| JP | 6-102016 | 4/1994 |
| JP | 7-23844 | 3/1995 |
| JP | 8-304694 | 11/1996 |

*Primary Examiner*—Hoa Q. Pham
(74) *Attorney, Agent, or Firm*—Frishauf, Holtz, Goodman & Chick, P.C.

(57) ABSTRACT

In an optical device having an objective lens for magnifying an image of a target object and a focusing unit including a laser source for irradiating the target object through the objective lens and a focus detecting light-receiving section for receiving light reflected from the target object, positions in the periphery of the target object are detected by using the laser beam emitted from the laser source of the focusing unit while changing a relative positional relationship between the target object and the objective lens.

18 Claims, 7 Drawing Sheets

METHOD AND APPARATUS FOR ALIGNING TARGET OBJECT

CROSS-REFERENCE TO RELATED APPLICATIONS

This is a Continuation-in-Part application of U.S. patent application Ser. No. 09/400,408, filed Sep. 21, 1999, the entire contents of which are incorporated herein by reference.

This application is based upon and claims the benefit of priority from the prior Japanese Patent Application No. 10-268301, filed Sep. 22, 1998, the entire contents of which are incorporated herein by reference.

BACKGROUND OF THE INVENTION

The present invention relates to a method and apparatus for aligning a target object such as a semiconductor wafer.

A wafer inspection apparatus for detecting, for example, defects in semiconductor wafers adjusts, before inspection, the position of the center of each wafer placed on a mount table for inspection.

There is a conventional wafer inspection apparatus of this type, in which while an edge of a wafer placed on a mount table is pushed by centering means such as a pin, or while the wafer edge is held by chuck means, the wafer is moved toward the axis of rotation of the mount table to align the center of the wafer with the axis of rotation of the table, thereby detecting wafer's orientation flat or notch on the basis of an output from a photoelectric sensor including a light emitting unit and a light receiving unit that are arranged such that a portion of the edge of a rotating wafer crosses their optical axis, and positioning the wafer such that the detected orientation flat or notch will be situated in a predetermined position.

However, where the centering means or chuck means that contacts an edge portion of a wafer is used, there is a probability that the wafer will be damaged by a shock applied thereto or contaminated as a result of being rubbed by the mount table. Furthermore, the photoelectric sensor, which is formed of the light emitting unit and the light receiving unit arranged such that an edge portion of each wafer crosses their optical axis, is provided as a unit dedicated to detect the orientation flat or the notch of each wafer. Therefore, the structure of the entire apparatus is inevitably complicated, and hence is very expensive.

BRIEF SUMMARY OF THE INVENTION

Accordingly, it is an object of the present invention to provide a method and apparatus for aligning a target object, that can detect the center of a target object such as a wafer, without touching the wafer and which can be manufactured to be compact and at low cost.

According to one aspect of the invention, there is provided an apparatus for aligning a target object, comprising: an objective lens for magnifying an image of the target object; focusing means including a laser source for irradiating the target object through the objective lens and a focus detecting light-receiving section for receiving light reflected from the target object, the focusing means being used for detecting a defocus from a detection result of the focus detecting light-receiving section to execute focusing; displacing means for changing a relative positional relationship between the target object and the objective lens such that a laser beam is emitted from the laser source of the focusing means to at least three points of a periphery of the target object; edge detecting means for detecting edge positions corresponding to at least three points excluding an orientation flat or a notch in the periphery of the target object, using the laser beam emitted from the laser source of the focusing means; and operating means for calculating a central position of the target object based on the edge positions detected by the edge detecting means.

The apparatus may further comprise control means for positioning the target object based on a result of the operating means.

In the apparatus, the edge detecting means may include a receiving section, provided on a different side of the target object from the objective lens and close to the periphery of the target object, for receiving light passing the target object.

In the apparatus, the receiving section may include a condenser lens for condensing the laser beam emitted from the objective lens and a photodiode for outputting an electric signal corresponding to an amount of the condensed laser beam.

In the apparatus, the edge detecting means may include a receiving section for receiving light reflected by the target object via the objective lens.

In the apparatus, the edge detecting means may detect an edge based on a variation of amounts of light in the focus detecting light-receiving section of the focusing means.

The apparatus may further comprise selecting means for selectively validating a function of the edge detecting section and invalidating a focusing function of the focusing means.

In the apparatus, the focusing means may be an autofocus unit into which the laser source and the focus detecting light-receiving section are integrally incorporated as one component.

In the apparatus, the focus detecting light-receiving means of the focusing means may include a plurality of light-receiving elements, and the edge detecting means may detect an edge based on a value obtained by adding signals generated from the plurality of light-receiving elements.

In the apparatus, the plurality of light-receiving elements may be used in detecting a focal point according to a confocal method.

In the apparatus, the plurality of light-receiving elements may be used in detecting a focal point according to a pupil split method.

In the apparatus, the plurality of light-receiving elements may be used in detecting a focal point according to an astigmatism method.

According to another aspect of the present invention, there is provided a method of aligning a target object applied to an optical device having an objective lens for magnifying an image of the target object, the method comprising the steps of: stopping a focusing function of an autofocus unit; irradiating the target object with a laser beam from a laser source provided in the autofocus unit through the objective lens while varying a relative positional relationship between the target object and the objective lens; detecting edge positions corresponding to at least three points excluding an orientation flat or a notch in a periphery of the target object, based on a variation of amounts of light reflected from the target object in a focus detecting light-receiving section provided in the autofocus unit; calculating a central position of the target object based on the detected edge portions; and positioning the target object based on the calculated central position.

In the method, in the edge position detecting step, an edge may be detected based on a value obtained by adding signals generated from a plurality of light-receiving elements constituting the focus detecting light-receiving section.

In the method, the autofocus unit may detect a focal point according to a confocal method.

In the method, the autofocus unit may detect a focal point according to a pupil split method.

In the method, the autofocus unit may detect a focal point according to an astigmatism method.

In the method, in the central position calculating step, coordinates of the central position may be acquired using a formula for a circle.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The embodiments of the invention will be described with reference to the accompanying drawings.

First Embodiment

Figure 1:
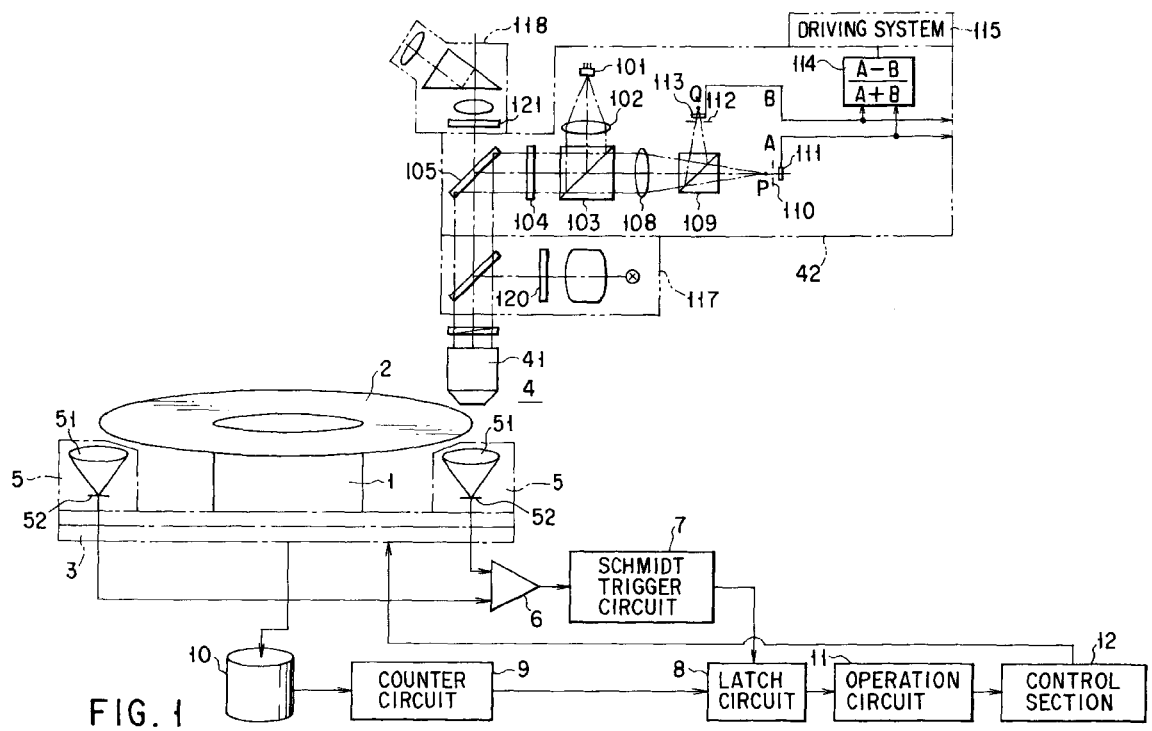
FIG. 1 is a schematic view illustrating a first embodiment of the invention.
Figure 2:
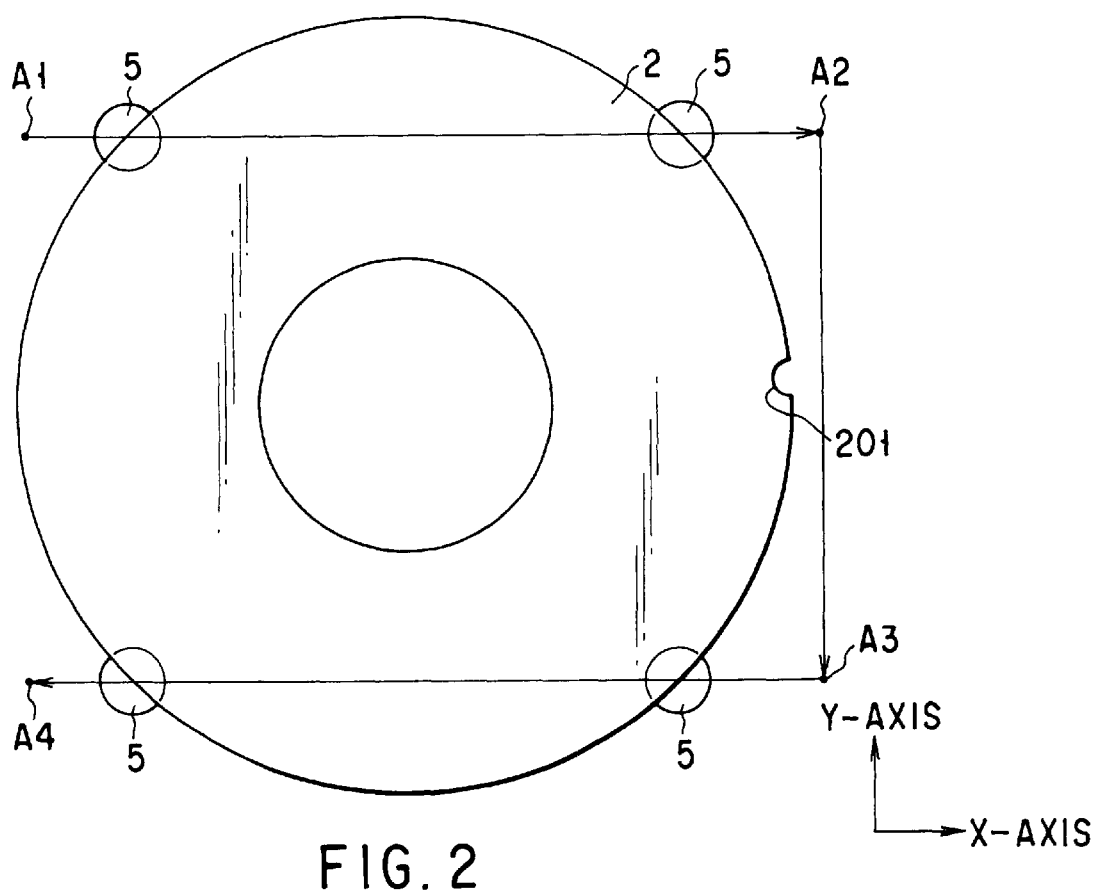
FIG. 2 is a view useful in explaining the operation of the first embodiment.

FIGS. 1 and 2 show a schematic structure of a wafer positioning apparatus to which the invention is applied. FIG. 1 is a side view, while FIG. 2 is a plan view. This wafer positioning apparatus is applied to an optical instrument (a wafer inspection microscope) provided with an autofocusing (AF) unit for automatically focusing a light beam on the surface of a wafer. In other words, the AF unit installed in the wafer inspection microscope is utilized for position detection of a wafer.

In FIG. 1, reference numeral 1 denotes a rotary table for holding a wafer 2. The rotary table 1 is provided on an XY stage 3, and movable in X- and Y-directions together with the XY stage 3.

A light projecting portion 4 that constitutes part of a photoelectric sensor is opposed to the surface of the wafer 2. The light projecting portion 4 includes a microscope-side objective lens 41 (i.e., an objective lens for magnifying an image of the target object such as a specimen) for guiding therethrough a light beam from a semiconductor laser light source 101 incorporated in an AF unit 42, and is disposed to radiate the surface of the wafer 2 with a light beam from the AF unit 42 in the shape of a spot. Suppose that in this embodiment, the objective lens 41 is fixed in a predetermined position apart from the surface of the wafer 2.

The wafer inspecting microscope main body used in the embodiment includes the light projecting portion 4 having the objective lens 41 and a light projection tube 117 for reflected illumination, the AF unit 42, a lens barrel 118 having an eyepiece, etc.

A light beam emitted from the semiconductor laser light source 101 incorporated in the AF unit 42 is converted into parallel light by a collimator lens 102, reflected by a deflection beam splitter 103, guided through a quarter-wave plate 104, reflected by a dichroic mirror 105, and emitted through the objective lens 41.

Various methods such as a pupil split method and an astigmatism method are proposed as a method for detecting a focal point. Any of the methods can be applied to the present invention. In the first embodiment, however, a confocal method is adopted, in which a focal point is detected by receiving the reflected light, which is divided by the beam splitter into components which pass in two directions, by two light-receiving elements arranged in different positions. This confocal method is disclosed by, e.g., Jpn. Pat. Appln. KOKAI Publication No. 8-304694.

That is, the reflected light having entered the objective lens 41 from the wafer 2 again passes through the dichroic mirror 105, the quarter-wave plate 104, the deflection beam splitter 103 and an image forming lens 108 in this order, and is divided by a beam splitter 109 into components which pass in two directions. One of the divided light components is guided to a first light receiving element (photodetector) 111 via a first aperture 110 located behind, by a distance L, the focal point P of the image forming lens 108. The other light component is guided to a second light receiving element (photodetector) 113 via a second aperture 112 located behind, by a distance L, the focal point Q of an image forming lens 108.

The first light receiving element 111 and the second light receiving element 113 generate electric signals A and B corresponding to the respective amounts of light that they received, and output them to a signal processing system 114.

On the basis of the electric signals A and B, the signal processing system 114 performs an operation of (A−B)/(A+B) (or an operation of A−B) to detect a focal point.

Figure 9:
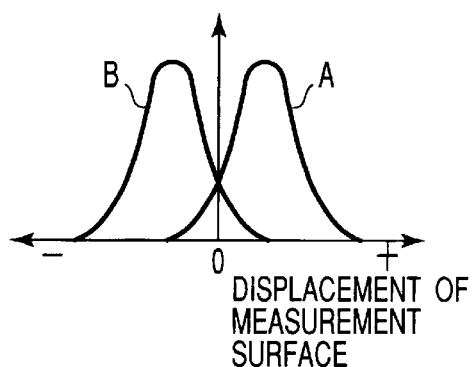
FIG. 9 is a graph showing a relationship between displacement of a measurement surface and an output of a light-receiving element in the second embodiment.
Figure 10:
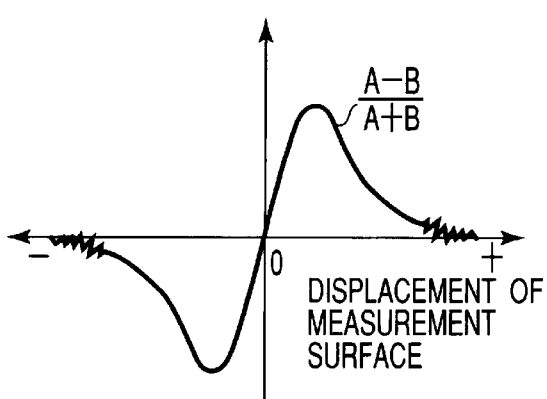
FIG. 10 is a graph showing a relationship between displacement of a measurement surface and a result of an operation.

FIG. 9 is a graph showing a relationship between displacement of a measurement surface and an output of the light-receiving elements. FIG. 10 is a graph showing a relationship between displacement of the measurement surface and a result of the above operation.

The signal processing system 114 performs the above operation to generate a signal that indicates a difference between a target value (=0) and an actual value as the operation result. A driving system 115 drives the AF unit 42 for focusing on the basis of the difference signal.

The electric signals A and B can also be used for detecting an edge of the wafer as in the second embodiment described below.

On the other hand, on the XY stage 3 near the wafer 2, there is provided four light receiving elements 5 for detecting the laser light beam guided via the aforementioned light projecting portion 4 from the semiconductor laser light source 101 incorporated in the AF unit 42. In this case, the light receiving elements 5 are provide on a concentric circle having the same radius of the wafer 2 from a rotary center of the rotary table 1. It is desirable that each light receiving unit 5 should be located at a distance from the wafer 2, at which the light receiving unit 5 is close to the wafer 3 keeping out of contact with the wafer 2, in particular, at a distance of 2–3 mm. Thus, the wafer 2 and each light receiving unit 5 are out of contact with each other, and the influence of light diffracted from the edge of the wafer 2 can be prevented.

Each light receiving unit 5 has a condenser lens 51 and a photodiode 52, and is arranged to condense, by the condenser lens 51, a light beam having passed through the objective lens 41, and then to receive it by the photodiode 52, thereby outputting, as a sensor signal, an electric signal corresponding to the amount of the received light.

Furthermore, where the center of the wafer 2 is situated at substantially the center of the rotary table 1, the light receiving units 5 are arranged as shown in FIG. 2 such that a linear line connecting the two of the units 5 lined in the X-axis direction of the XY stage 3 is parallel to the X-axis of the XY stage 3, while a linear line connecting the two of the units 5 lined in the Y-axis direction of the XY stage 3 is parallel to the Y-axis of the XY stage 3, and further such that the same area of the light receiving surface of each light receiving unit 5 is shaded with an edge portion of the wafer 2.

A Schmidt trigger 7 is connected to the photodiode 52 of each light receiving unit 5 via an OP amplifier circuit 6. The Schmidt trigger circuit 7 outputs a pulse signal having its waveform shaped when the output of each light receiving unit 5 rises and falls.

The Schmidt trigger circuit 7 is connected to a latch circuit 8, which is connected to a rotary encoder 10 via a counter circuit 9.

The rotary encoder 10 is attached to the shaft of a motor (not shown) for driving the X-axis of the XY stage 3, and detects the X-axis directional position of the XY stage 3. The counter circuit 9 outputs a count value corresponding to the X-axis directional stage position detected by the rotary encoder 10. The latch circuit 8 latches and stores the count value of the counter circuit 9 at the time of falling or rising of the output of each light receiving unit 5 having its waveform shaped by the Schmidt trigger circuit 7.

An operation circuit 11 calculates four points of the edge portion of the wafer 2 on the basis of the count values stored in the latch circuit 8, thereby calculating the position of the center of the wafer 2.

A control section 12 controls the AF unit 42 so as to stop a focusing function of the AF unit 42 and detect an edge of the wafer. In other words, when the control section 12 detects the edge, it selectively validates the edge detecting function (the latch circuit 8, operation circuit 11, and the like) and invalidates the focusing function (the signal processing system 114 and driving system 115) of the AF unit 42.

The control section 12 adjusts the position of the wafer 2 by driving the stage, on the basis of the wafer center coordinates calculated by the operation circuit 11.

The operation of the embodiment constructed as above will be described.

First, the wafer 2 is taken from a wafer cassette by a transfer machine or a transfer robot, and then placed on the rotary table 1 on the XY stage 3 that is mounted on a microscope, in order to perform microscopic observation such as outward appearance inspection.

Subsequently, the XY stage 3 with the wafer mounted thereon is moved in a state in which the position of the objective lens 41 of the microscope constituting the light projecting portion 4 is fixed. In other words, the XY stage 3 is moved to scan the wafer 2 with a light beam guided through the objective lens 41 from the semiconductor laser light source 101 incorporated in the AF unit 42.

More specifically, first, the XY stage 3 is moved such that the relative position of the objective lens 41 opposed to the wafer 2 moves in the X-axis direction from a position A1 (which is near the upper left light receiving unit 5 but away from the same unit 5) to a position A2 (which is near the upper right light receiving unit 5 but away from the same unit 5).

At this time, the light beam emitted from the semiconductor laser light source 101 incorporated in the AF unit 42 is vertically applied to the wafer 2 via the objective lens 41. When the objective lens 41 is situated in the position A1 detached from the upper left light receiving unit 5, the light beam does not reach the photodiode 52 of the light receiving unit 5, and hence a sensor signal from the photodiode 52 is at an L level, as is shown in FIG. 3A.

Figure 3A:
FIGS. 3A and 3B are other views useful in explaining the operation of the first embodiment.

After the objective lens 41 reaches a position above the light receiving unit 5, and hence the light beam reaches the photodiode 52 of the light receiving unit 5, the sensor signal of the photodiode 52 changes to an H level as indicated by B1 of FIG. 3A. After that, the light beam is shaded by an edge portion of the wafer 2, and the sensor signal of the photodiode 52 again changes to the L level. At this time, the position of the edge portion of the wafer 2 is detected at the moment of occurrence of an edge indicated by the arrow at B1 in the figure.

After that, the objective lens reaches a position above the upper right light receiving unit 5 in FIG. 2, where the light beam is not shaded with an edge portion of the wafer 2, and reaches the photodiode 52 of the light receiving unit 5. At this time, the sensor signal of the photodiode 52 again changes to the H level as indicated by the arrow at B2 of the figure. Thereafter, the light beam left the light receiving unit 5 and reaches the point A2 near the light receiving unit 5, where the sensor signal of the photodiode 52 again changes to the L level. At this time, the position of the edge portion of the wafer 2 is detected at the moment of occurrence of an edge indicated by the arrow at B2 in the figure.

The latch circuit 8 latches the count value of the counter circuit 9, using the trailing edge of the H level at B1 and the rising edge of the H level at B2, which are included in sensor signal variations shown in FIG. 3A caused with the movement of the XY stage 3. In other words, the latch circuit 8 stores a count value corresponding to a stage position detected by the rotary encoder 10 when the light beam is shaded with an edge portion of the wafer 2, and a count value corresponding to a stage position detected by the rotary encoder 10 when the light beam is not shaded with an edge portion of the wafer 2.

Then, the XY stage 3 is moved so that the position of the objective lens 41 relative to the wafer 2 will be shifted in the Y-axis direction to in a point A3 (which is near the lower right light receiving unit 5 but away from the same unit 5 ) in FIG. 2, and then the stage 3 is moved so that the relative position is shifted in the X-direction to a point A4 (which is near the lower left light receiving unit 5 but away from the same unit 5) in FIG. 2.

Figure 3B:
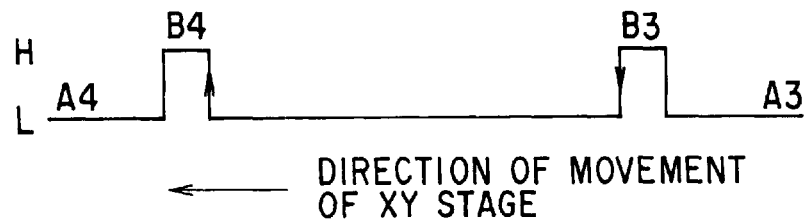

Also in this case, the sensor signal of the photodiode 52 becomes H level at points B3 and B4 in FIG. 3B, as in the above-described case, and the latch circuit 8 latches the count value of the counter circuit 9, using the trailing edge of the H level at B3 and the rising edge of the H level at B4, which are included in sensor signal variations shown in FIG. 3B. In other words, the latch circuit 8 stores a count value corresponding to a stage position detected by the rotary encoder 10 when the light beam is shaded with an edge portion of the wafer 2, and a count value corresponding to a stage position detected by the rotary encoder 10 when the light beam is not shaded with an edge portion of the wafer 2. The count value is supplied to the operation circuit 11.

Since the Y-axis coordinate corresponding to the X-axis coordinate of each of the above-obtained edge points of the wafer 2 is already known, the X-axis and Y-axis coordinates of the four edge points at which the light beam is shaded can be calculated.

To calculate the position of the center of the wafer 2 from the X-axis and Y-axis coordinates of the four edge points, data on optional three points, which do not include the orientation flat or the notch, is selected, and the coordinate values of the three points are substituted into the formula for a circle, thereby calculating the coordinate of the center of the wafer 2.

If the XY coordinate data of the four points do not contain the influence of the orientation flat or notch, four combinations of wafer center coordinates obtained from optional three points of the four points have the same values. Accordingly, any wafer center coordinates may be used. However, if one of the four points contains the influence of the orientation flat or notch, three of the four combinations of wafer center coordinates are false wafer center coordinates due to the orientation flat or notch. In this case, it is necessary to detect the XY coordinate data item that contains the orientation flat or notch, and then to calculate the center coordinates of the wafer 2 from the XY coordinates of the three points except for the XY coordinate data item that contains the orientation flat or notch.

As described above, the first embodiment employs the light projecting portion 4 for projecting a light beam from the semiconductor laser light source 101 incorporated in the AF unit 42 onto the surface of the wafer 2, and the four light receiving units 5 for detecting a change in the intensity of the light beam having passed through the wafer 2, thereby detecting four edge portions of the wafer to obtain the center coordinates of the wafer, from changes in the intensity of the light beam received by each light receiving unit 5 while the wafer 2 is moved together with the XY stage 3. Accordingly, the wafer center coordinates can be obtained without touching the wafer, which means that the wafer center positioning can be executed without damaging or contaminating the wafer surface.

Further, since a light beam from the semiconductor laser light source 101 incorporated in the AF unit 42 is used as that of the light projecting portion 4, and no new structural element is added for obtaining a light beam, the apparatus can have a simple structure and be made compact at low cost.

Moreover, since the wafer center position is obtained on the basis of that one of position data items concerning edge portions of the wafer detected by the four light receiving units 5, which is not influenced by the orientation flat or the notch, the wafer center can be calculated accurately.

In addition, the use of a transmission type photoelectric sensor consisting of the light projecting portion 4 and the light receiving units 5 enables detection of a wafer edge portion independent of the state of the wafer surface.

Furthermore, the wafer position detecting apparatus can be mounted on the XY stage 3 for an optical instrument such as a wafer inspecting microscope that has the AF unit 42.

Although in the first embodiment, the photo-electric sensor is used only to detect the edge of the wafer 2, the orientation flat or the notch can be detected using one of the light receiving units 5. In this case, where the above-described center position detection has been executed, one of the light receiving units 5 is made to correspond to the light projecting portion 4, thereby rotating the wafer 2. It should be noted that the shape of a notch portion 201 or an orientation flat 202 is standardized. Consider a sensor signal output from the photodiode 52 of each light receiving unit 5 and corresponding to the notch 201. Where an edge portion of the wafer 2 overlaps the spot of the light beam guided from the objective lens 41, the sensor signal is kept constant at the L level, whereas it increases (to the H level) immediately after the beam leaves the edge portion of the wafer 2, i.e. the beam reaches the notch portion 201. This means that the position of the notch portion 201 can be detected by detecting an edge portion of the wafer 2 at which the sensor signal of the photodiode 52 shows the maximum level (H level). In this case, an exclusive light projecting portion for detecting the orientation flat or the notch may be prepared.

It is desirable that the condenser lens 51 which constitutes each light receiving unit 5 should have a slightly large diameter in light of, for example, the safety of transfer of the wafer 2 to the rotary table 1 mounted on the XY stage 3.

Second Embodiment

Figure 4:
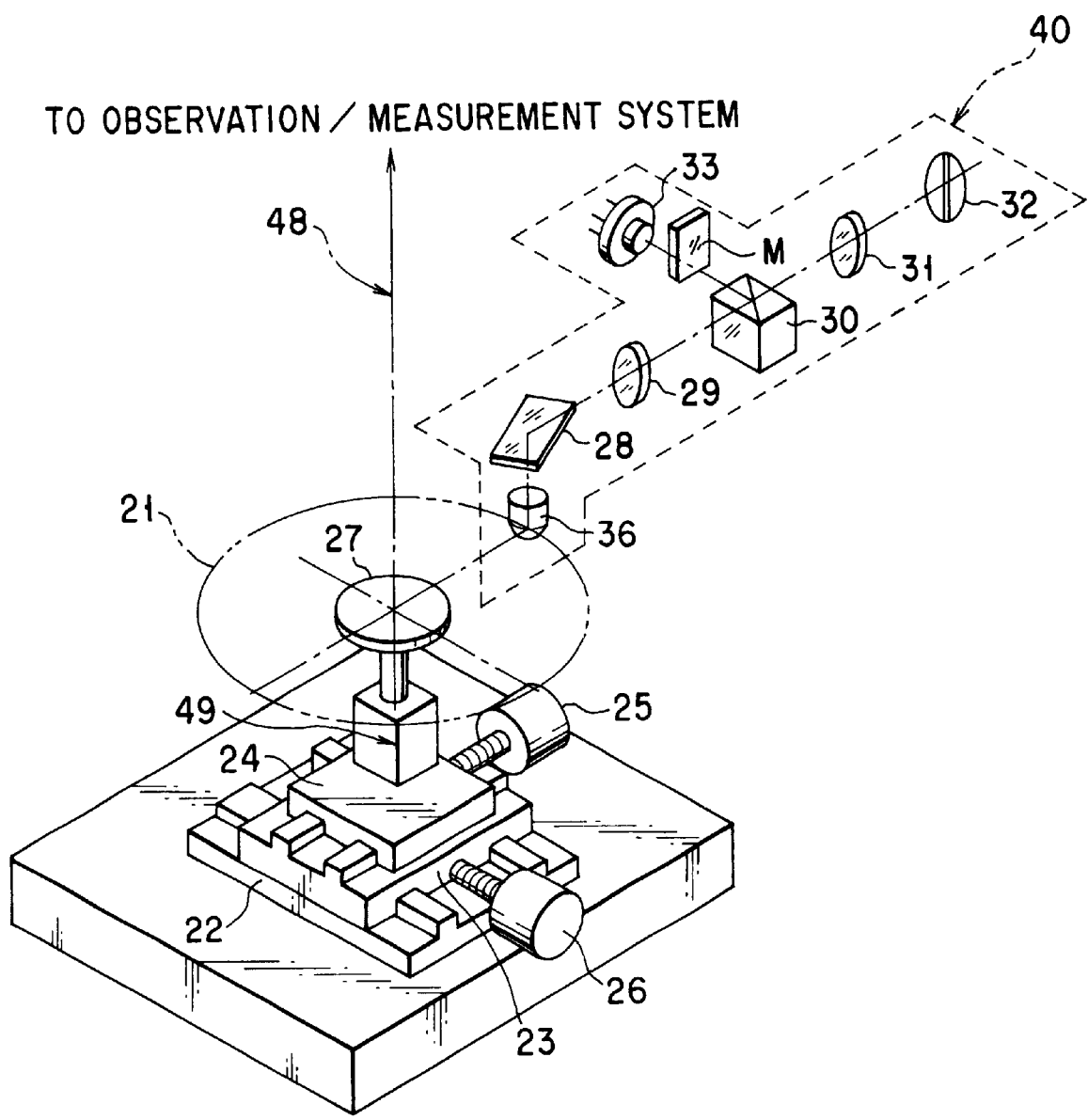
FIG. 4 is a schematic view showing a second embodiment of the invention.

FIG. 4 is a perspective view showing a schematic structure of a second embodiment of the invention.

In this case, reference numeral 22 denotes an XY stage, which has a structure wherein an X-axis directionally movable X stage 24 is stacked on a Y-axis directionally movable Y stage 23. The stages 24 and 23 are connected to an X pulse motor 25 and a Y pulse motor 26, respectively. The X pulse motor 25 and the Y pulse motor 26 are arranged to be able to be moved, by ball screws, perpendicular to the X stage 24 and the Y stage 23, respectively, thereby enabling detection of the movement amounts (e.g. the number of pulses) of the X stage 24 and the Y stage 23 with respect to their respective reference positions. The obtained movement amounts are sent to an operation circuit 38.

The X stage 24 has a rotary table 27. A wafer 21 is placed on the rotary table 27, where the position of the notch can be adjusted.

Various methods such as a pupil split method and an astigmatism method are proposed as a method for detecting a focal point. Any of the methods can be applied to the present invention. In the second embodiment, however, the pupil split method (two-piece splitting method) is adopted. This pupil split method is disclosed by, e.g., Jpn. Pat. Appln. KOKAI Publication No. 6-102016.

Figure 5:
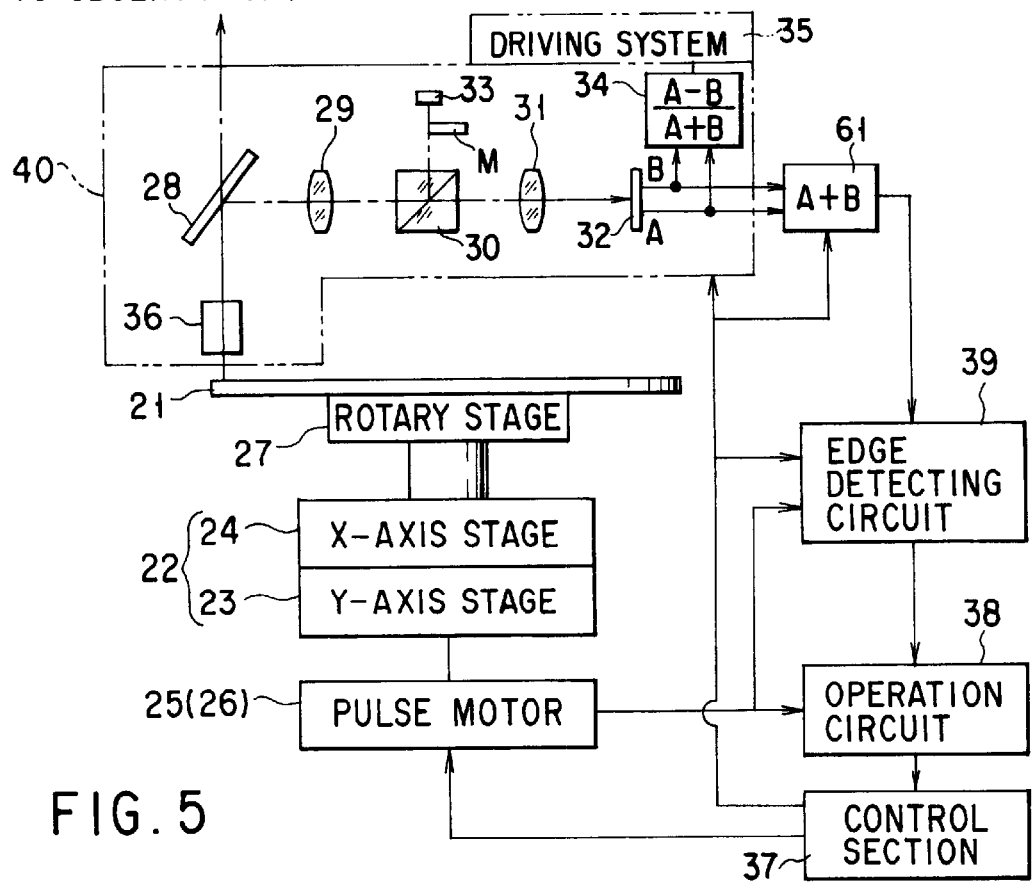
FIG. 5 is another schematic view showing the second embodiment of the invention.

That is, in FIGS. 4 and 5, half the light emitted from the semiconductor laser light source 33 in the AF unit 40 is shielded by a light shield M disposed in the light path. The light not shielded is reflected by the PBS 30 and converged onto the wafer 21 via the image forming lens 29, the DM 38 and the objective lens 36. The light reflected from the wafer 21 is guided through the path in the opposite direction and converged onto the two-piece PD 32 via the image forming lens 31.

The two-piece PD 32 is constituted of two photoelectric converting elements, and the light detected thereby is converted to electric signals A and B. In response to the signals A and B, a signal processing system 34 performs an operation of (A−B)/(A+B) (or an operation of A−B) to detect a focal point.

Figures 11A, 11B, 11C:
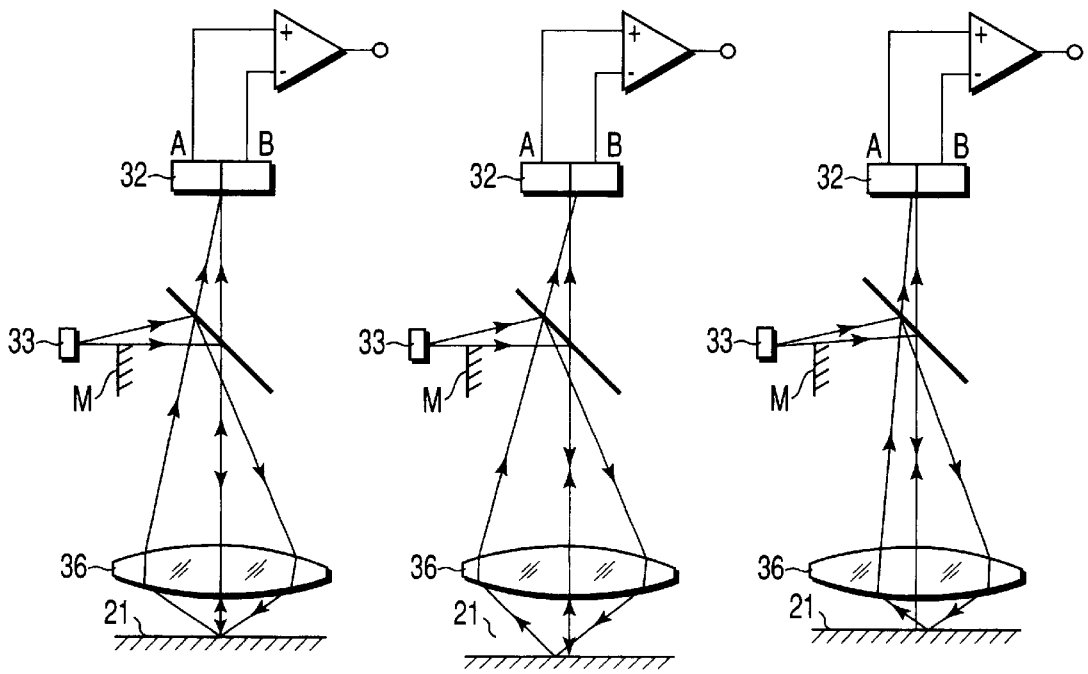
FIGS. 11A to 11C are diagrams useful in explaining a pupil split method.
Figure 12A:
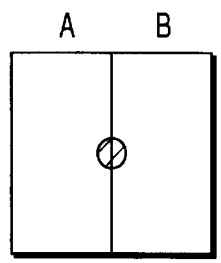
FIGS. 12A to 12C are diagrams useful in explaining the pupil split method.
Figure 12B:
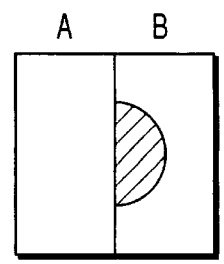
Figure 12C:
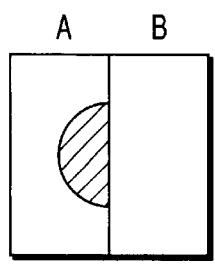

When the wafer 21 is located in a focal point as a sample, an image is formed in the center of the two-piece PD 32 as illustrated in FIGS. 11A and 12A and thus the above operation result is 0. When the wafer 21 is located far from the focal point, an image is formed on side B of the two-piece PD 32 as illustrated in FIGS. 11B and 12B and thus the above operation result is smaller than 0. When the wafer 21 is located close to the focal point, an image is formed on side A of the two-piece PD 32 as illustrated in FIGS. 11C and 12C and thus the above operation result is larger than 0. The relationship between the displacement of the measurement surface and the operation results is the same as that in the graph shown in FIG. 10.

A signal processing system 34 performs the above operations to generate a signal that indicates a difference between a target value (=0) and an actual value as the operation results. A driving system 35 drives the AF unit 40 for focusing in response to the difference signal.

Another signal processing system 61 is provided to detect an edge of the wafer 21. Upon receiving the signals A and B from the two-piece PD 32, the system 61 adds them and sends a value of A+B to an edge detection circuit 39 as a result of the addition. The signal processing system 61 can be provided in the edge detection circuit 39 or the AF unit 40. Without the system 61, the value of A+B obtained from the signal processing system 34 can directly be supplied to the edge detection circuit 39.

Figure 13:
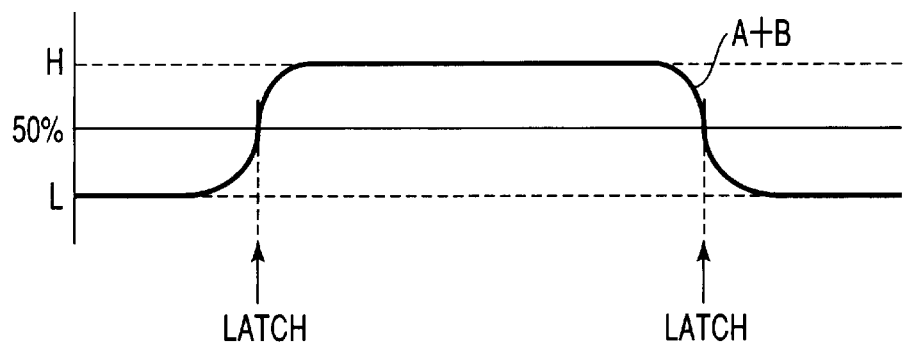
FIG. 13 is a diagram useful in explaining an edge detecting method in the second embodiment.

An edge detection circuit 39 detects an edge of the wafer 21 based on the value of A+B. Specifically, the circuit 39 has functions corresponding to the counter circuit and latch circuit described above. When the value of A+B reaches an intermediate value (50%) between H and L levels during the movement of the XY stage 22 as shown in FIG. 13, the edge detection circuit 39 generates a latch signal and detects an edge position of the wafer 21. The information of the edge position is transmitted to the operation circuit 38.

The edge detection circuit 39 calculates a central position of the wafer 21 based on the edge position information transmitted from the edge detection circuit 39 and an amount of displacement of the X and Y stages 24 and 23 obtained from the X and Y pulse motors 25 and 26.

A control section 37 controls the AF unit 40 so as to stop a focusing function of the AF unit 40 and detect an edge of the wafer. In other words, when the control section 37 detects the edge, it selectively validates the edge detecting function (the edge detection circuit 39, the signal processing system 61, and the like) and invalidates the focusing function (the signal processing system 34 and driving system 35) of the AF unit 40.

The control section 37 adjusts the position of the wafer 21 by driving the stage, on the basis of the wafer center coordinates calculated by the operation circuit 38.

In the second embodiment, the pupil split method is employed to detect a focal point using the AF unit. However, the present invention is not limited to this method. For example, as explained in the first embodiment, the confocal method can be instead employed in which a focal point is detected by receiving the reflected light, which is divided by the beam splitter into components which pass in two directions, by two light-receiving elements arranged in different positions and, in this case, too, a value of A+B can be obtained from electric signals A and B generated from the light-receiving elements and sent to the edge detection circuit to thereby detect an edge of the wafer.

The astigmatism method (four-piece splitting method) can be adopted in place of the above method. In the astigmatism method, a cylindrical lens is disposed in an optical path to provide the optical system with astigmatism, and a detector detects a variation of the section of luminous flux due to the displacement of the measurement surface from the focal point. This astigmatism method is disclosed by, e.g., Jpn. Pat. Appln. KOKAI Publication No. 7-23844.

Figures 14A, 14B, 14C:
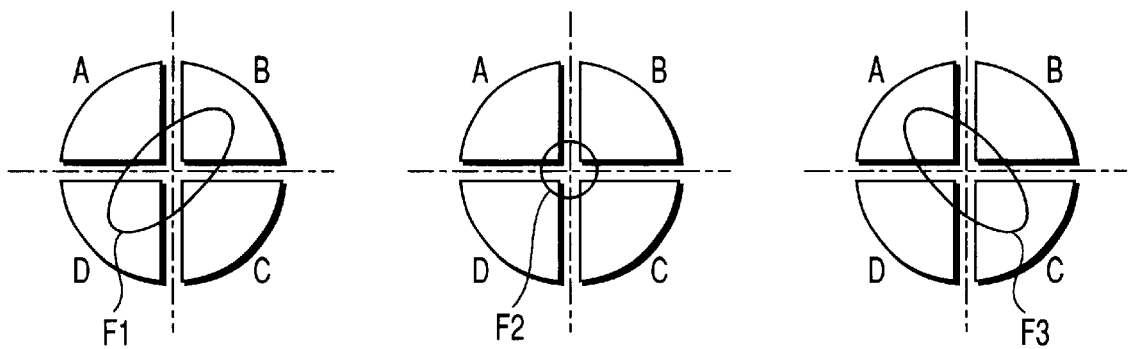
FIGS. 14A to 14C are views useful in explaining an astigmatism method.
Figure 15:
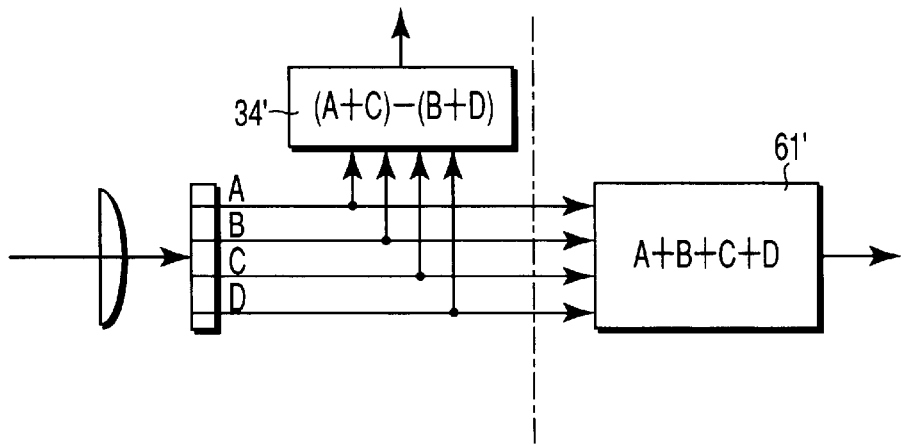
FIG. 15 is a view showing a structure adopting the astigmatism method.

That is, if the optical system has astigmatism, a focal-point image varies in shape on the four-piece split light-receiving element as indicated by F1 to F3 in FIGS. 14A to 14C. In the AF unit, as illustrated in FIG. 15, electric signals A to D are generated form four pieces of the light-receiving element and, based on these signals, a signal processing system 34' performs an operation of (A+C)−(B+D) to detect a focal point. In this case, another signal processing system 61' performs an operation of A+B+C+D from electric signals A to D generated from the light receiving element and sends the value to the edge detection circuit to detect an edge of the wafer.

The operation of the embodiment constructed as above will now be described.

First, the control section 37 stops the focusing function of the AF unit 40 before detecting an edge of the wafer. Subsequently, the control section 37 validates the edge detecting function (the edge detection circuit 39, the signal processing system 61, and the like), and performs the following edge detecting process.

Figure 6:
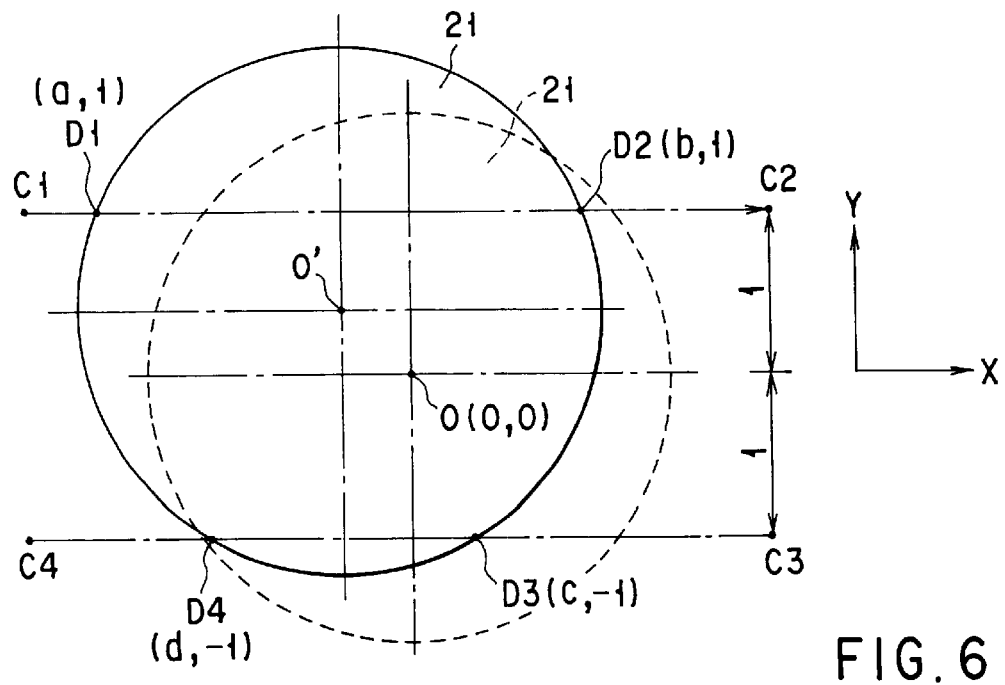
FIG. 6 is a view useful in explaining the operation of the second embodiment.

Also in this case, in a manner similar to that described in the first embodiment, the X stage 24 and the Y stage 23 are independently moved in the X-axis and Y-axis directions, respectively, to thereby move a light beam from the objective lens 36 of the AF unit 40. As a result, the position of the objective lens 36 is moved relative to the wafer 21 in the order of C1, C2, C3 and C4 as shown in FIG. 6.

The edge detecting circuit 39 detects, from the outputs of the two-piece PD 32, a rising point D1 and a falling point D2 of a signal that indicates light reflected from the wafer 21 and is obtained while the wafer is moved from C1 to C2, and also a rising point D3 and a falling point D4 of a signal that indicates light reflected from the wafer 21 and is obtained while the wafer is moved from C3 to C4. Thus, the coordinate data of the edges D1–D4 of the wafer 21 can be obtained. In this case, the coordinate data of each edge D1–D4 is obtained on the basis of a movement amount per one pulse of driving pulses for the X pulse motor 25 and the Y pulse motor 26 that move the objective lens 36 relative to the wafer 21 in the order of C1, C2, C3 and C4.

Supposing that the obtained coordinates are D1 (a, 1), D2 (b, 1), D3 (c, −1) and D4 (d, −1), these coordinate data items are supplied to the operation circuit 38, where calculation is performed to obtain the center of the wafer 21.

In the following calculations, a case where no orientation flat or notch overlaps the points D1–D4 is supposed.

A formula for a circle is given by $$(x-x')^2 + (y-y')^2 = r^2 x - x' \tag{1}$$

Since the coordinates of each edge D1–D4 of the wafer 21 satisfy the equation (1), the following equations are obtained when the coordinates are substituted in the equation (1):

$$(a-x')^2 + (1-y')^2 = r^2$$
$$(b-x')^2 + (-1-y')^2 = r^2$$
$$(c-x')^2 + (-1-y')^2 = r^2$$
$$(d-x')^2 + (131\ y')^2 = r^2 \tag{2}$$

Accordingly, the following answers are obtained:

$$x' = (a+d)/2 \tag{3}$$
$$= (b+c)/2$$
$$Y' = 1 - \{r^2 - ((a-d)/2)\}^{-2}$$
$$= 1 + \{r^2 - ((b-c)/2)\}^{-2}$$

Accordingly, supposing that the center position of the wafer 21 placed on the rotary table 27 of the XY stage 22 manually or by transfer means is 0' (x', y') as shown in FIG. 5, the difference between the center position 0' and the center 0 (0, 0) of the wafer 21 indicated by the broken line and obtained when the axis-of-rotation 49 of the rotary table 27 coincides with an observation/measurement axis 48, i.e. a displacement of the center position of the wafer 21 from an ideal position, can be expressed by $$\Delta x = x' - x_0 \tag{4}$$
$$= \{(a+d)/2\} - x_0$$
$$= \{(b+c)/2\} - x_0$$
$$\Delta y = y' - y_0$$
$$= 1 - \{r^2 - ((a-d)/2)\}^{-2} - y_0$$
$$= -1 + \{r^2 - ((b-c)/2)\}^{-2} - y_0$$

Even if in this case, the notch of the wafer 21 overlaps one of the edges D1–D4 of the wafer 21, and this state is detected, a displacement of the center position of the wafer 21 can be calculated in the manner described above, using the three points other than the point that overlaps the notch.

Although in the above description, the photoelectric sensor is used to detect a displacement of the center position of the wafer 21, it can be used to detect the position of the notch. In this case, the rotary table 27 is rotated with the center position of the wafer 21 corrected.

Figure 7:
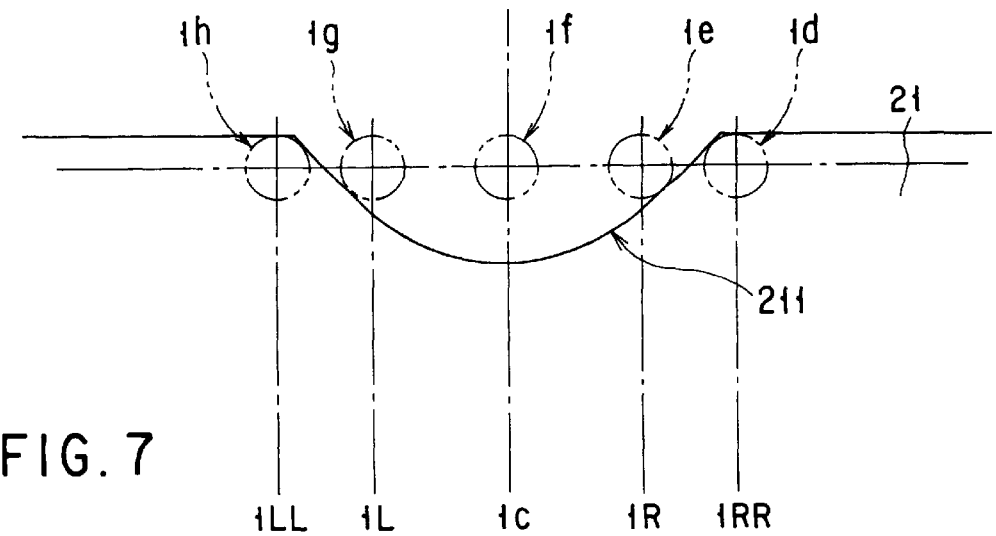
FIG. 7 is another view useful in explaining the operation of the second embodiment.

The shape of a notch portion 211 shown in FIG. 7 and generally employed in the wafer 21 is standardized. Further, consider the output of the two-piece PD 32 of the AF unit 40 corresponding to the notch 211 of the wafer 21. The amount of light reflected from the wafer 21 becomes zero immediately after the light leaves the edge portion of the wafer 2, i.e. when it reaches the notch portion 211. This means that the position of the notch portion 211 can be detected by detecting an edge portion where the amount of reflected light becomes zero, while catching edge signals at edge portions of the wafer 21 by the focusing operation of the AF unit 40.

More specifically, since the amount of movement corresponding to one pulse of driving pulses output to the driving pulse motor for driving the rotary table 27 is already known, the position of the notch portion 211 can be detected from the states of the edge signals indicating light beams 1*h*, 1*g*, 1*f*, 1*e* and 1*d* corresponding to positions 1LL, 1L, 1C, 1R and 1RR shown in FIG. 7.

Accordingly, a similar advantage to that obtained in the first embodiment can be expected from the above structure, and further, the detecting means for detecting the amount of light reflected from the surface of the wafer 21 uses the two-piece PD 32 of the AF unit 40 to receive light reflected from the wafer 21. In other words, the two-piece PD serves as both the photodiode and the detecting means, thereby simplifying the structure of the apparatus, enabling reduction of the size of the apparatus, and reducing its manufacturing cost.

Moreover, since the light receiving units are not provided on the XY stage side, differing from the first embodiment, the space can be more effectively used.

Figure 8:
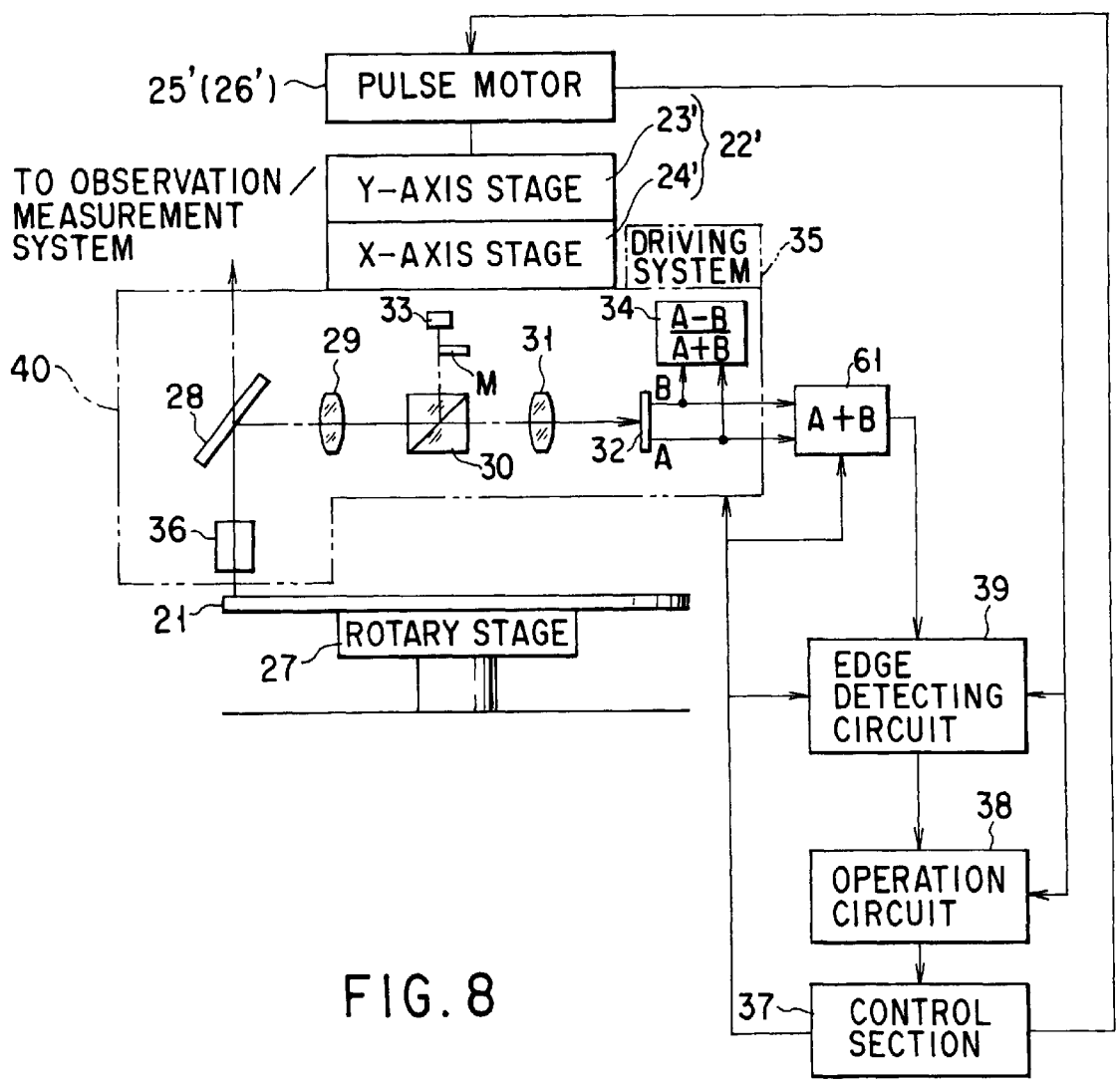
FIG. 8 is a view illustrating a modification of the structure shown in FIG. 5.

Furthermore, although in the FIG. 5 structure, the XY stage 22 and the pulse motor 25 (26) are provided on the rotary table 27 side to move the XY stage 22 (together with the wafer 21) with the AF unit 40 fixed, this structure may be replaced with a structure as shown in FIG. 8, in which an XY stage 22' and a pulse motor 25' (26') are provided on the AF unit 40 side to move the AF unit 40 with the wafer 21 fixed. Alternatively, an X-axis stage and a Y-axis stage may be provided on the rotary table 27 side and on the AF unit 40 side, respectively.

As described above, in the invention, a light beam from focusing means is projected onto a wafer surface, and wafer displacing means is controlled to move the wafer in directions perpendicular to each other while detecting changes in the amount of the light beam reflected from the wafer surface, thereby detecting at least three edge portions of the wafer, which do not contain the orientation flat or the notch of the wafer, and positioning the wafer by the wafer displacing means on the basis of the detected edge portions. Thus, the center of the wafer can be calculated and positioned without touching the wafer.

Further, since the light beam from the AF unit is used, no particular structural element for obtaining the light beam is necessary.

Also, since the amount of the light beam reflected from the wafer surface can be detected by one detection means, the structure of the apparatus can be more simplified.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for aligning a target object, comprising:
   an objective lens for magnifying an image of the target object;
   focusing means including a laser source for irradiating the target object through the objective lens and a focus detecting light-receiving section for receiving light reflected from the target object, the focusing means being used for detecting a defocus from a detection result of the focus detecting light-receiving section to execute focusing;

displacing means for changing a relative positional relationship between the target object and the objective lens such that a laser beam is emitted from the laser source of the focusing means to at least three points of a periphery of the target object;

a rotary table for holding the target object;

edge detecting means for detecting edge positions corresponding to at least three points excluding an orientation flat or a notch in the periphery of the target object, using the laser beam emitted from the laser source of the focusing means; and operating means for calculating a displacement of a central position of the target object from an axis-of-rotation position of the rotary table based on the edge positions detected by the edge detecting means.

2. The apparatus according to claim 1, further comprising control means for positioning the target object based on a result of the operating means.

3. The apparatus according to claim 1, wherein the edge detecting means includes a receiving section, provided on a different side of the target object from the objective lens and close to the periphery of the target object, for receiving light passing the target object.

4. The apparatus according to claim 3, wherein the receiving section includes a condenser lens for condensing the laser beam emitted from the objective lens and a photodiode for outputting an electric signal corresponding to an amount of the condensed laser beam.

5. The apparatus according to claim 1, wherein the edge detecting means includes a receiving section for receiving light reflected by the target object via the objective lens.

6. The apparatus according to claim 1, wherein the edge detecting means detects an edge based on a variation of amounts of light in the focus detecting light-receiving section of the focusing means.

7. The apparatus according to claim 6, further comprising selecting means for selectively validating a function of the edge detecting section and invalidating a focusing function of the focusing means.

8. The apparatus according to claim 1, wherein the focusing means is an autofocus unit into which the laser source and the focus detecting light-receiving section are integrally incorporated as one component.

9. The apparatus according to claim 1, wherein the focus detecting light-receiving means of the focusing means includes a plurality of light-receiving elements, and the edge detecting means detects an edge based on a value obtained by adding signals generated from the plurality of light-receiving elements.

10. The apparatus according to claim 9, wherein the plurality of light-receiving elements is used in detecting a focal point according to a confocal method.

11. The apparatus according to claim 9, wherein the plurality of light-receiving elements is used in detecting a focal point according to a pupil split method.

12. The apparatus according to claim 9, wherein the plurality of light-receiving elements is used in detecting a focal point according to an astigmatism method.

13. A method of aligning a target object applied to an optical device having an objective lens for magnifying an image of the target object, the method comprising the steps of:

stopping a focusing function of an autofocus unit;

irradiating the target object with a laser beam from a laser source provided in the autofocus unit through the objective lens while varying a relative positional relationship between the target object and the objective lens;

detecting edge positions corresponding to at least three points excluding an orientation flat or a notch in a periphery of the target object, based on a variation of amounts of light reflected from the target object in a focus detecting light-receiving section provided in the autofocus unit;

calculating a central position of the target object based on the detected edge portions; and positioning the target object based on the calculated central position.

14. The method according to claim 13, wherein in the edge position detecting step, an edge is detected based on a value obtained by adding signals generated from a plurality of light-receiving elements constituting the focus detecting light-receiving section.

15. The method according to claim 14, wherein the autofocus unit detects a focal point according to a confocal method.

16. The method according to claim 14, wherein the autofocus unit detects a focal point according to a pupil split method.

17. The method according to claim 14, wherein the autofocus unit detects a focal point according to an astigmatism method.

18. The method according to claim 14, wherein in the central position calculating step, coordinates of the central position is acquired using a formula for a circle.

* * * * *